US010741296B2

(12) United States Patent
Sasaki et al.

(10) Patent No.: US 10,741,296 B2
(45) Date of Patent: Aug. 11, 2020

(54) IMAGING TABLE AND RADIATION IMAGING SYSTEM

(71) Applicant: CANON KABUSHIKI KAISHA, Tokyo (JP)

(72) Inventors: Yoshito Sasaki, Kawasaki (JP); Tomoaki Ichimura, Kawasaki (JP); Shinichi Takeda, Kawasaki (JP); Kota Nishibe, Kawasaki (JP); Tomohiro Hoshina, Kawasaki (JP); Akiya Nakayama, Kawasaki (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 30 days.

(21) Appl. No.: 16/175,354

(22) Filed: Oct. 30, 2018

(65) Prior Publication Data

US 2019/0139666 A1 May 9, 2019

(30) Foreign Application Priority Data

Nov. 9, 2017 (JP) .................................. 2017-216311

(51) Int. Cl.
*A61B 6/04* (2006.01)
*G21K 1/02* (2006.01)
*A61B 6/06* (2006.01)
*A61B 6/00* (2006.01)

(52) U.S. Cl.
CPC ............ *G21K 1/025* (2013.01); *A61B 6/0407* (2013.01); *A61B 6/06* (2013.01); *A61B 6/4266* (2013.01); *A61B 6/4283* (2013.01); *A61B 6/4452* (2013.01); *A61B 6/4291* (2013.01)

(58) Field of Classification Search
CPC ........ G21K 1/025; A61B 6/0407; A61B 6/06; A61B 6/4266; A61B 6/4283; A61B 6/4452; A61B 6/4291
USPC ......................................... 378/154, 208, 209
See application file for complete search history.

(56) References Cited

U.S. PATENT DOCUMENTS

| 6,341,893 B1 * | 1/2002 | Matsumoto .......... G03B 42/025 378/195 |
| 7,256,404 B2 | 8/2007 | Inoue et al. |
| 7,391,029 B2 | 6/2008 | Takeda et al. |
| 7,514,686 B2 | 4/2009 | Ogawa et al. |
| 7,595,493 B2 | 9/2009 | Okada et al. |

(Continued)

FOREIGN PATENT DOCUMENTS

| JP | 2001-327484 A | 11/2001 |
| JP | 2010-264054 A | 11/2010 |

(Continued)

OTHER PUBLICATIONS

U.S. Appl. No. 15/757,693, Katsuro Takenaka, filed Mar. 6, 2018.
U.S. Appl. No. 16/043,340, Takamasa Ishii, filed Jul. 24, 2018.
U.S. Appl. No. 16/150,523, Eriko Sato, filed Oct. 3, 2018.

*Primary Examiner* — Courtney D Thomas
(74) *Attorney, Agent, or Firm* — Venable LLP

(57) ABSTRACT

An imaging table includes: a bucky apparatus to which a radiation imaging apparatus capable of being installed; a top plate connected to the bucky apparatus and allowing a subject to get on the top plate; and a rotation mechanism arranged to connect the bucky apparatus and the top plate in a relatively rotatable manner. The imaging table of the present invention can easily correspond to a plurality of imaging techniques.

12 Claims, 7 Drawing Sheets

(56) References Cited

U.S. PATENT DOCUMENTS

| | | |
|---|---|---|
| 7,714,294 B2 | 5/2010 | Sawada et al. |
| 7,723,693 B2 | 5/2010 | Okada et al. |
| 7,777,167 B2 | 8/2010 | Takeda et al. |
| 7,952,058 B2 | 5/2011 | Nomura et al. |
| 8,115,177 B2 | 2/2012 | Takeda et al. |
| 8,304,735 B2 | 11/2012 | Inoue et al. |
| 8,440,975 B2 | 5/2013 | Inoue et al. |
| 8,648,312 B2 | 2/2014 | Ichimura et al. |
| 8,653,463 B2 | 2/2014 | Sawada et al. |
| 8,653,465 B2 | 2/2014 | Nagano et al. |
| 8,704,185 B2 | 4/2014 | Ishida et al. |
| 8,957,383 B2 | 2/2015 | Sasaki et al. |
| 9,006,665 B2 | 4/2015 | Nagano et al. |
| 9,052,400 B2 | 6/2015 | Saruta et al. |
| 9,054,012 B2 | 6/2015 | Nomura et al. |
| 9,081,104 B2 | 7/2015 | Sawada et al. |
| 9,354,333 B2 | 5/2016 | Inoue et al. |
| 9,366,767 B2 | 6/2016 | Inoue et al. |
| 9,529,094 B2 | 12/2016 | Ishii et al. |
| 2012/0219115 A1 | 8/2012 | Okada et al. |
| 2013/0020493 A1 | 1/2013 | Ishii et al. |
| 2013/0153775 A1 | 6/2013 | Nomura et al. |
| 2013/0168559 A1 | 7/2013 | Saruta et al. |
| 2013/0187054 A1 | 7/2013 | Ishii et al. |
| 2013/0221198 A1 | 8/2013 | Sawada et al. |
| 2013/0308755 A1 | 11/2013 | Ishida et al. |
| 2014/0034836 A1 | 2/2014 | Takei et al. |
| 2014/0091225 A1 | 4/2014 | Sasaki et al. |
| 2014/0151769 A1 | 6/2014 | Wayama et al. |
| 2016/0097865 A1 | 4/2016 | Sasaki et al. |
| 2016/0172414 A1 | 6/2016 | Saruta et al. |
| 2016/0181308 A1 | 6/2016 | Ichimura et al. |
| 2016/0270755 A1 | 9/2016 | Takenaka et al. |
| 2017/0285189 A1 | 10/2017 | Ryu et al. |
| 2018/0070906 A1 | 3/2018 | Terui et al. |
| 2018/0136343 A1 | 5/2018 | Terui et al. |

FOREIGN PATENT DOCUMENTS

| | | |
|---|---|---|
| JP | 2016-187380 A | 11/2016 |
| JP | 2016-189984 A | 11/2016 |

* cited by examiner

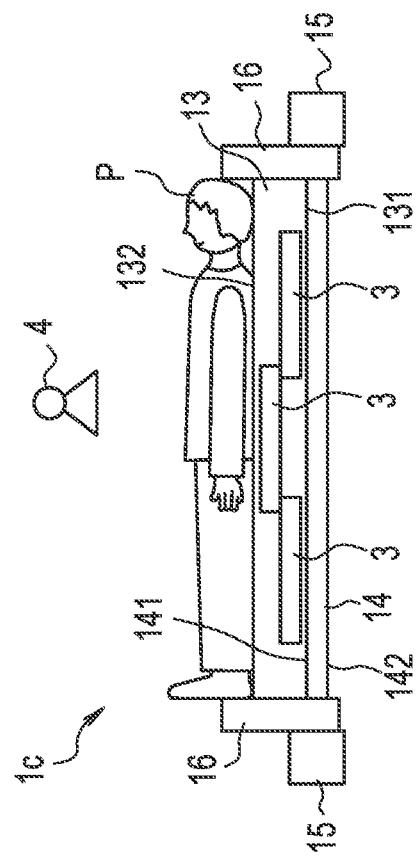
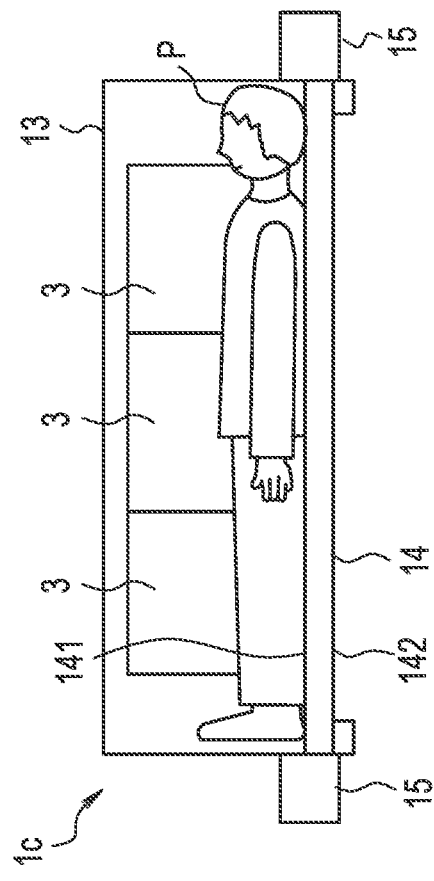
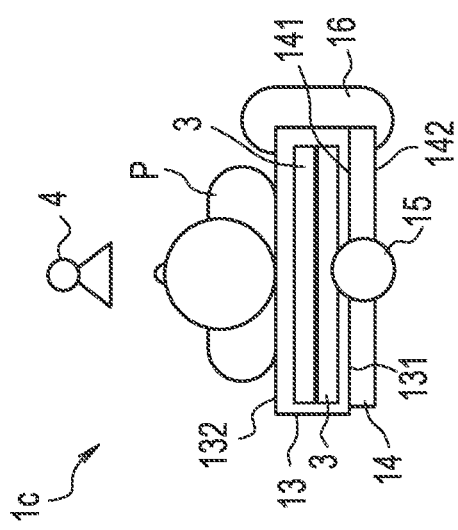
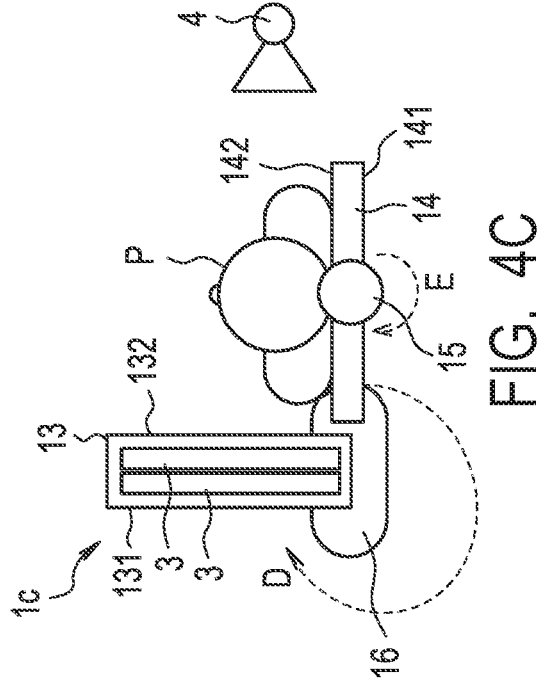

IMAGING TABLE AND RADIATION IMAGING SYSTEM

BACKGROUND OF THE INVENTION

Field of the Invention

The present invention relates to an imaging table and a radiation imaging system.

Description of the Related Art

As a method for radiation imaging of a comparatively wide range, such as the upper half or lower half of the body of a human subject (subject), the so-called one shot long-length imaging, i.e., an imaging method that performs imaging with one time radiation irradiation by using a plurality of radiation imaging apparatuses is performed. Japanese Patent Application Laid-Open No. 2016-189984 discloses, as an apparatus used for the one shot long-length imaging, an apparatus that can perform imaging for a standing position and a recumbent position. Japanese Patent Application Laid-Open No. 2016-187380 discloses a method of using apparatuses corresponding to a standing position, a recumbent position, and a lateral recumbent position.

Incidentally, when performing radiation imaging of, for example, a patient with lateral curvature, the imaging of a standing position, a recumbent position, and a lateral recumbent position is required. Further, among such imaging, there are imaging methods such as the traction imaging that performs imaging during a patient is pulling up and down, and the bolster imaging that performs imaging of a patient from the side surface in a state where the patient is lying on his/her back on a bed with a pillow to the thoracolumbar junction, so that the spinal column is stretched by the patient's own weight and respiratory relaxation is achieved. Since the apparatus corresponding to each body site and imaging method is required for the imaging, the corresponding apparatus and bed are required, and it was also necessary to provide a large installation space.

In view of the above-mentioned actual circumstances, one of the problems to be solved by the present invention is to enable corresponding to methods of radiation imaging, and to facilitate the setting corresponding to the methods of radiation imaging.

SUMMARY OF THE INVENTION

In order to solve the above-mentioned problem, an imaging table according to one embodiment of the present invention includes: a bucky apparatus to which a radiation imaging apparatus can be installed; a top plate connected to the bucky apparatus and allowing a subject to get on the top plate; and a rotation mechanism arranged to connect the bucky apparatus and the top plate to each other in a relatively rotatable manner.

Further features of the present invention will become apparent from the following description of exemplary embodiments with reference to the attached drawings.

BRIEF DESCRIPTION OF THE DRAWINGS

FIGS. 4A, 4B, 4C and 4D are schematic diagrams illustrating exemplary configurations of the imaging table according to a third embodiment.

DESCRIPTION OF THE EMBODIMENTS

Preferred embodiments of the present invention will now be described in detail in accordance with the accompanying drawings.

The imaging table according to each embodiment of the present invention can perform one shot long-length imaging of a human subject (patient, etc.) in a state where the imaging table is installed with a plurality of radiation imaging apparatuses. Additionally, the imaging table according to each embodiment corresponds to a plurality of imaging techniques including standing position imaging, recumbent position imaging, and lateral recumbent position imaging.

First Embodiment

Figure 1:
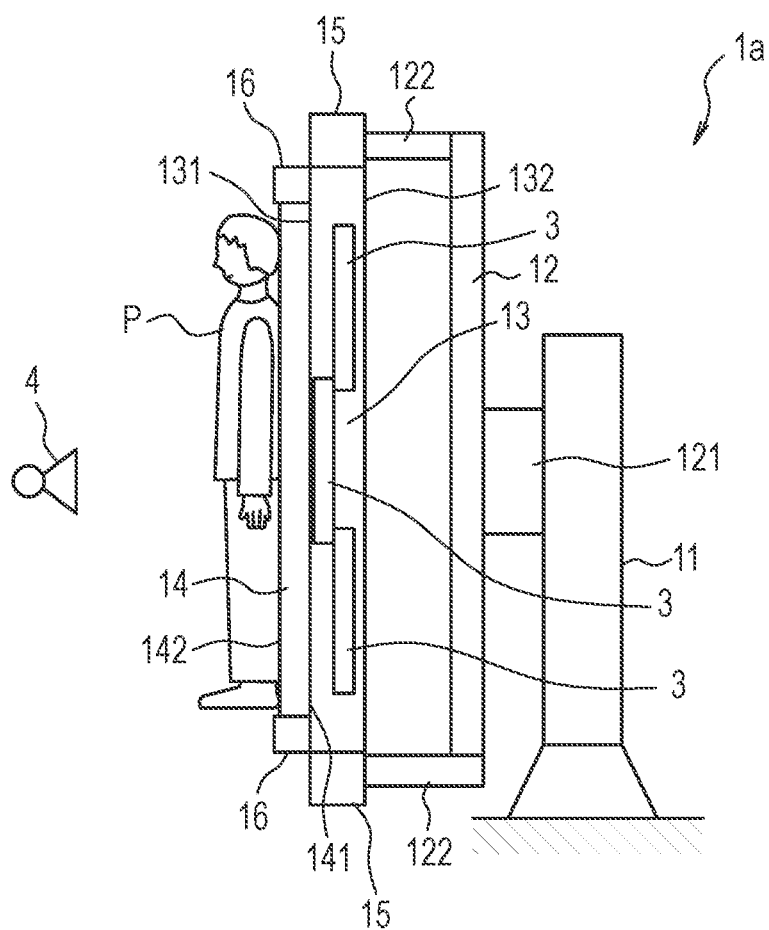
FIG. 1 is a schematic diagram illustrating an exemplary configuration of an imaging table according to a first embodiment.
Figure 2A:
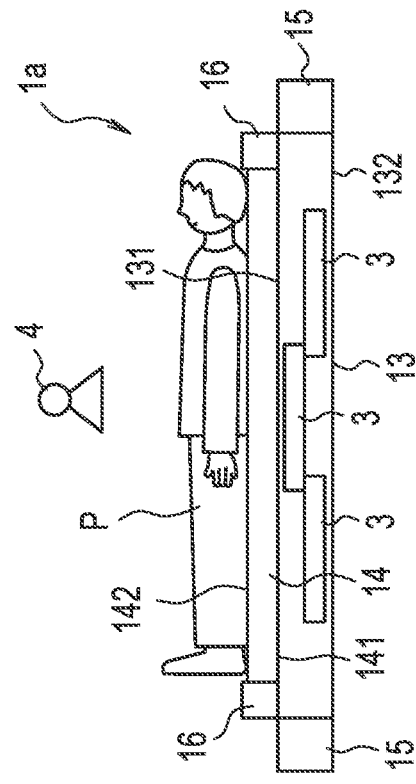
FIGS. 2A, 2B, 2C and 2D are schematic diagrams illustrating exemplary configurations of the imaging table according to the first embodiment.
Figure 2B:
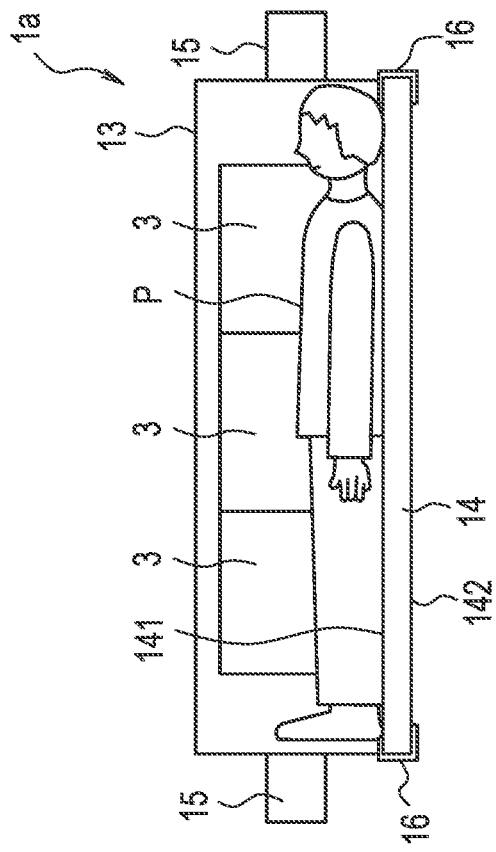
Figure 2C:
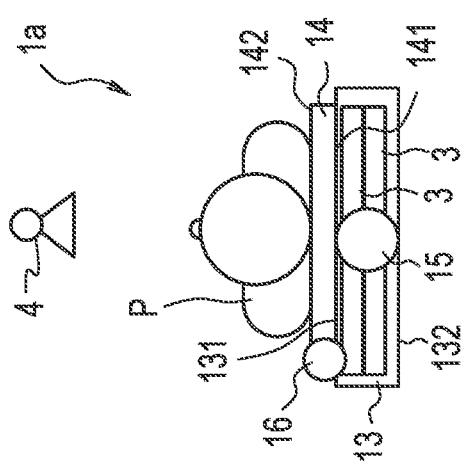
Figure 2D:
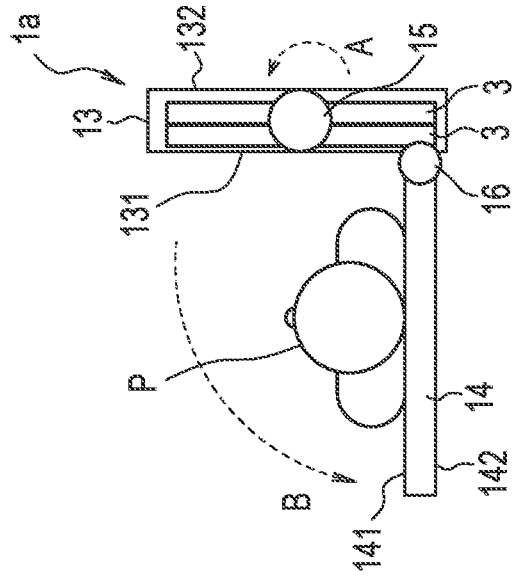

FIG. 1 is a diagram schematically illustrating an exemplary configuration of an imaging table 1a according to a first embodiment, and is a diagram schematically illustrating the setting of the imaging table 1a and the state of a human subject P (subject) in the case of performing the standing position imaging. FIGS. 2A to 2D are diagrams schematically illustrating the setting of the imaging table 1a and the state of the human subject P in the cases of performing the recumbent position imaging and the lateral recumbent position imaging by using the imaging table 1a according to the first embodiment. FIG. 2A and FIG. 2B are a transverse cross sectional view (a cross sectional view cut along a surface perpendicular to the long length direction of a top plate 14) and a vertical cross sectional view (a cross sectional view cut along a surface perpendicular to the short length direction of the top plate 14) in the case of performing the recumbent position imaging, respectively. FIG. 2C and FIG. 2D are a transverse cross sectional view and a vertical cross sectional view in the case of performing the lateral recumbent position imaging, respectively. As illustrated in FIG. 1, the imaging table 1a includes a support column 11, a support unit 12, a bucky apparatus 13, and the top plate 14. Note that, in FIGS. 2A to 2D, the support column 11 and the support unit 12 are omitted.

The support column 11 of the imaging table 1a is provided such that the support column 11 stands up perpendicularly on an installation surface (for example, a floor surface of a radiation imaging room, etc.) for the imaging table 1a. The support unit 12 is connected to (supported by) the support column 11 so as to be movable to the up-and-down direction and to be rotational. For example, the support unit 12 includes a rotary part 121, and two arms 122 integrally provided to this rotary part 121. The rotary part 121 of the support unit 12 is connected to (supported by) the support column 11 so as to be movable to the up-and-down direction, and to be rotatable about a horizontal axis (the irradiation direction of the radiation of a radiation source 4 at the time of the standing position imaging and the lateral recumbent position imaging) serving as the rotation center line. Therefore, the support unit 12 is rotatable by the rotary part 121 with the axis in the direction (the left-and-right direction in FIG. 1) perpendicular to the direction of a center line (the up-and-down direction in FIG. 1) of the relative rotation of the top plate 14 and the bucky apparatus 13 by a rotation mechanism 16 described later, the axis serving as the rotation center. Each of the two arms 122 of the support unit 12 is connected to a respective one of two supporters 15. Each of the two supporters 15 is connected to a respective one of the both ends of the long length direction of the bucky apparatus 13. Then, the two supporters 15 rotatably support the bucky apparatus 13 about a straight line passing through the two supporters 15 (for example, a straight line parallel to the long length direction of the bucky apparatus 13, and passing through the center of the short length direction of the bucky apparatus 13).

The bucky apparatus 13 has, for example, an elongated shape, includes a grid (Lysholm) for removing scattered rays and a mechanism for moving the grid, and is configured so that a plurality of portable-type radiation imaging apparatuses 3 (electronic cassettes) can be arranged and installed in the bucky apparatus 13. Additionally, the human subject P, who is the subject, can get on and lie down on the bucky apparatus 13. By arranging and installing the plurality of radiation imaging apparatuses 3 in the bucky apparatus 13, a long-length imaging can be performed by one time irradiation of radiation. Note that, in each figure, an example of the configuration in which three radiation imaging apparatuses 3 are arranged and installed in the bucky apparatus 13 is illustrated, neither the number of the radiation imaging apparatuses 3 that can be installed in the bucky apparatus 13, nor the positional relationship among the plurality of radiation imaging apparatuses 3 to be installed is particularly limited. For example, a configuration may be adopted that allows arrangement and installation of two radiation imaging apparatuses 3, or four or more radiation imaging apparatuses 3 may be arranged and installed. Additionally, a plurality of radiation imaging apparatuses 3 can be attached to and detached from the bucky apparatus 13, and the radiation imaging apparatus 3 can be reversed and installed in the bucky apparatus 13. For example, the radiation imaging apparatus 3 can be turned over (reversed) and installed in the bucky apparatus 13, depending on the posture of the human subject P in the imaging and the imaging direction.

The top plate 14 has, for example, an elongated plate-like configuration, and allows the human subject P, who is the subject, to get on and take a lying posture on the top plate 14. The top plate 14 can be formed such that the length of the top plate 14 may become shorter than the length of the bucky apparatus 13 in the long length direction and the short length direction. The top plate 14 is connected to the bucky apparatus 13 by the rotation mechanism 16. Therefore, the top plate 14 and the bucky apparatus 13 are relatively rotatable by this rotation mechanism 16. The specific configuration of the top plate 14 is not particularly limited, and a configuration similar to the top plate 14 of various kinds of known imaging apparatuses can be applied.

The rotation mechanism 16 connects the bucky apparatus 13 to the top plate 14 in a relatively rotatable manner. Note that the center line of relative rotation of the top plate 14 and the bucky apparatus 13 by this rotation mechanism 16 is parallel to the center line of relative rotation of the supporters 15 and the bucky apparatus 13, and is perpendicular to the center line of rotation of the support unit 12 with respect to the support column 11. Additionally, the rotation mechanism 16 can hold the bucky apparatus 13 and the top plate 14 to an arbitrary relative angle. Then, by relatively rotating the bucky apparatus 13 and the top plate 14 via the rotation mechanism 16, a change can be made to an arbitrary one of at least the following states, i.e., the state where the bucky apparatus 13 and the top plate 14 are overlapped on each other (see FIGS. 2A and 2B), and the state where the relative angle between the bucky apparatus 13 and the top plate 14 is 90 degrees (see FIGS. 2C and 2D). For example, the rotation mechanism 16 is arranged such that one long side (end portion) of the elongated shaped bucky apparatus 13 is connected to one long side (end portion) of the elongated shaped top plate 14. Then, the bucky apparatus 13 and the top plate 14 can be relatively rotated about the respective long sides located on the same side or about the vicinity of the long sides (the axis parallel to the long sides). Here, the bucky apparatus 13, the top plate 14, and the rotation mechanism 16 can be configured such that the total length of the top plate 14 and the rotation mechanism 16 is substantially equal to the length of the bucky apparatus 13 in the long length direction and the short length direction.

Note that, in FIGS. 2A to 2D, the configuration is illustrated in which the rotation mechanism 16 is provided in two places, but the number of the rotation mechanisms 16 is not particularly limited. For example, the configuration may be adopted in which the rotation mechanism 16 is provided in one place, or the configuration may be adopted in which the rotation mechanisms 16 are provided in three or more places. Additionally, the specific configuration of the rotation mechanism 16 is also not particularly limited. The rotation mechanism 16 may have a configuration that can connect the top plate 14 to the bucky apparatus 13 in a relatively rotatable manner, and can maintain the relative angle between the bucky apparatus 13 and the top plate 14 at an arbitrary angle.

Additionally, for convenience of description, as for each of both surfaces of the bucky apparatus 13, when the relative angle between the bucky apparatus 13 and the top plate 14 is 0 degree (see FIGS. 2A and 2B), the surface of the side facing the top plate 14 is called the first surface 131, and the surface of the opposite side is called the second surface 132. Similarly, as for each of both surfaces of the top plate 14, the surface of the side facing the bucky apparatus 13 is called the first surface 141, and the surface of the opposite side is called the second surface 142.

The configuration of the radiation imaging apparatus 3 that can be installed in the bucky apparatus 13 is not particularly limited. The bucky apparatus 13 may have a configuration that allows the arrangement and installation of a plurality of conventionally known various kinds of portable-type radiation imaging apparatuses 3. Additionally, the radiation imaging apparatus 3 can be installed in the bucky apparatus 13 such that an incident surface (a surface turned to the upstream side of the incident radiation at the time of imaging) of the radiation imaging apparatus 3 is positioned on the first surface 131 side, and on the second surface 132 side.

When performing the standing position imaging of the human subject P by using the imaging table 1a, as illustrated in FIG. 1, the bucky apparatus 13 and the top plate 14 are set such that their long length directions become parallel to the up-and-down direction. Further, the setting is made such that the second surface 142 of the top plate 14 faces to the radiation source 4 side in the state where the bucky apparatus 13 and the top plate 14 are overlapped on each other. That is, the relative angle between the bucky apparatus 13 and the top plate 14 is set to be 0 degree. As described above, the bucky apparatus 13 is supported by the supporters 15 connected to the support unit 12, and the support unit 12 is rotatably connected to the support column 11. Therefore, the long length directions of the bucky apparatus 13 and the top plate 14 can be made parallel to the up-and-down direction by rotating the bucky apparatus 13 and the top plate 14 together with the support unit 12 about the axis in the horizontal direction. Additionally, the state in which the bucky apparatus 13 and the top plate 14 are overlapped on each other (the state where the relative angle between the bucky apparatus 13 and the top plate 14 is 0 degree) can be set by relatively rotating the bucky apparatus 13 and the top plate 14 via the rotation mechanism 16. Note that the radiation source 4 is arranged such that radiation can be irradiated towards the top plate 14 and the bucky apparatus 13 (such that the optical axis of the radiation becomes perpendicular to the second surface 142 of the top plate 14). When the setting is made in this way, the standing position imaging of the human subject P standing along the second surface 142 of the top plate 14 can be performed.

When performing the recumbent position imaging, as illustrated in FIGS. 2A and 2B, the setting is made such that the top plate 14 overlaps on the upper side of the bucky apparatus 13, and the second surface 142 of the top plate 14 is substantially horizontal and faces to the upper direction. Specifically, the support unit 12 is set in the orientation in which the straight line passing through the two supporters 15 becomes horizontal, and the bucky apparatus 13 is set in the orientation to be horizontal. Further, the setting is made such that the relative angle between the top plate 14 and the bucky apparatus 13 is 0 degree, and the top plate 14 overlaps on the upper side of the bucky apparatus 13. Then, the radiation source 4 is arranged above the bucky apparatus 13 and the top plate 14 such that the radiation source 4 can downwardly irradiate the radiation (such that the optical axis of the radiation becomes perpendicular to the second surface 142 of the top plate 14). When the setting is made in this way, the recumbent position imaging can be performed on the human subject P on the second surface 142 (the top surface) of the top plate 14.

When performing the lateral recumbent position imaging, as illustrated in FIGS. 2C and 2D, the top plate 14 is set such that the first surface 141 is substantially horizontal and faces to the upper direction, and the bucky apparatus 13 is set such that the first surface 131 becomes perpendicular. Specifically, the support unit 12 is set in the orientation in which the straight line passing through the two supporters 15 become horizontal. The bucky apparatus 13 is set in the orientation in which its first surface 131 become perpendicular, and the rotation mechanism 16 is arranged in the lower side (the long side of the bucky apparatus 13 on the side to which the rotation mechanism 16 is connected is located in the lower side, and the long side of the bucky apparatus 13 becomes horizontal). The top plate 14 is set in the orientation in which the first surface 141 is substantially horizontal and faces to the upper direction. That is, the angle formed by the top plate 14 and the bucky apparatus 13 is set to be 90 degrees. Then, the radiation source 4 is arranged such that the optical axis of the radiation becomes horizontal and perpendicular to the first surface 131 of the bucky apparatus 13, so as to be able to irradiate the radiation towards the first surface 131 of the bucky apparatus 13. When the setting is made in this way, the lateral recumbent position imaging can be performed on the human subject P on the first surface 141 of the top plate 14.

Note that, in order to change the setting from the recumbent position imaging illustrated in FIGS. 2A and 2B to the lateral recumbent position imaging illustrated in FIGS. 2C and 2D, the bucky apparatus 13 may be rotated 90 degrees such that the side provided with the rotation mechanism 16 is located in the lower side, and the top plate 14 may be rotated 90 degrees with respect to the bucky apparatus 13. An arrow A in FIG. 2C indicates the rotation direction of the bucky apparatus 13, and an arrow B indicates the rotation direction of the top plate 14. In this case, in either of the recumbent position imaging and the lateral recumbent position imaging, since the radiation is made incident from the first surface 131 side of the bucky apparatus 13, the radiation imaging apparatus 3 to be installed in the bucky apparatus 13 may not be reversed. In this way, according to the first embodiment, the setting can be changed between the recumbent position imaging and the lateral recumbent position imaging by rotating the bucky apparatus 13 with respect to the support unit 12, and rotating the top plate 14 with respect to the bucky apparatus 13. However, while the human subject P gets on the second surface 142 of the top plate 14 in the recumbent position imaging, the human subject P gets on the first surface 141 of the top plate 14 in the lateral recumbent position imaging. Thus, getting off and getting on by the human subject P is required.

As described above, according to the imaging table 1a according to the first embodiment, the standing position imaging, and the recumbent position imaging and the lateral recumbent position imaging can be performed by rotating the bucky apparatus 13 with respect to the support column 11. Then, the setting can be changed to arbitrary setting of the recumbent position imaging setting and the lateral recumbent position imaging setting by relatively rotating the bucky apparatus 13 and the top plate 14 to change the relative angle. On this occasion, the radiation imaging apparatus 3 to be installed in the bucky apparatus 13 may not be reversed (the radiation imaging apparatus 3 may not be removed and inserted again). Thus, the change of setting becomes easy, and the effort and time required for the preparation (the change of setting) of imaging can be omitted and reduced, respectively. Additionally, since the top plate 14 has the function of a bed on which the human subject P who is the subject lies, another bed may not be provided separately. Accordingly, auxiliary equipment such as a bed can be reduced, and the space for the installation place (an imaging room, etc.) for the imaging table 1a can be saved.

Second Embodiment

Figure 3B:
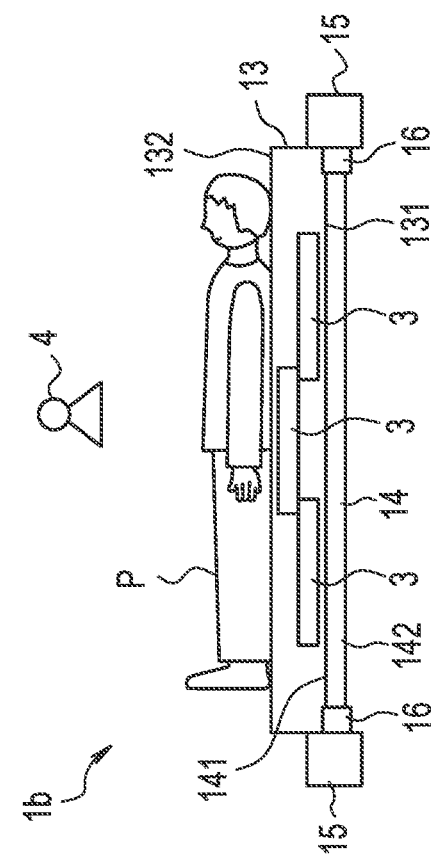
FIGS. 3A, 3B, 3C and 3D are schematic diagrams illustrating exemplary configurations of the imaging table according to a second embodiment.
Figure 3D:
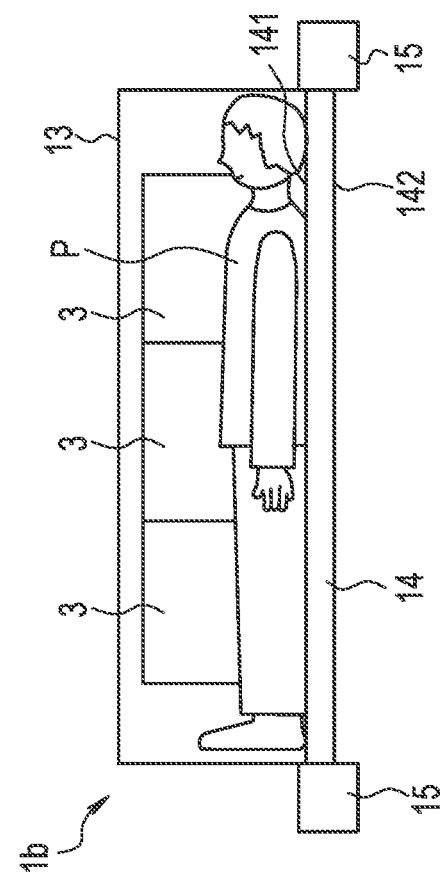
Figure 3A:
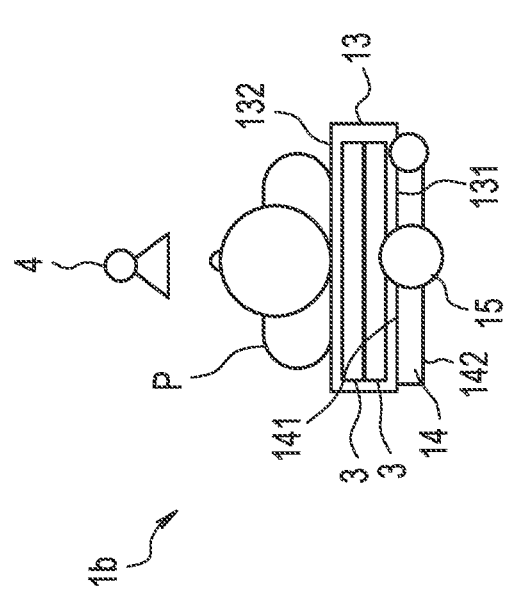
Figure 3C:
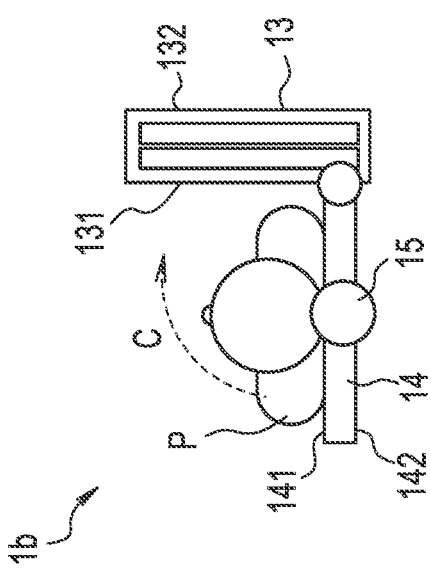

As for the configurations that are common to or can be made common to the first embodiment, the reference numerals same as those in the first embodiment are used, and their descriptions are omitted (the same applies to third to fifth embodiments). FIGS. 3A to 3D are diagrams schematically illustrating the setting of an imaging table 1b according to a second embodiment and the state of the human subject P in the case of performing the recumbent position imaging and in the case of performing the lateral recumbent position imaging by using the imaging table 1b. FIG. 3A and FIG. 3B are a transverse cross sections and a vertical cross sectional view in the case of performing the recumbent position imaging, respectively. FIG. 3C and FIG. 3D are a transverse cross sectional view and a vertical cross sectional view in the case performing the lateral recumbent position imaging, respectively.

In the imaging table 1b according to the second embodiment, the top plate 14 is connected to the two supporters 15. For example, the top plate 14 has an elongated shape, and each of both ends in the long length direction is connected to a respective one of the two supporters 15. Then, the top plate 14 can be rotated about an axis passing through the two supporters 15 (a straight line passing through the center of the short length direction of the top plate 14, and parallel to the long length direction). Additionally, the bucky apparatus 13 and the top plate 14 are connected via the rotation mechanism 16 as in the first embodiment, and they can be relatively rotated.

When performing the standing position imaging by using the imaging table 1b, the bucky apparatus 13 and the top plate 14 are set such that their long length directions become parallel to the up-and-down direction. Further, the bucky apparatus 13 and the top plate 14 are set to overlap on each other with the relative angle between them being 0 degree. Then, the second surface 132 of the bucky apparatus 13 is set to be oriented toward the radiation source 4 side. For example, the state is achieved in which the positions of the bucky apparatus 13 and the top plate 14 are interchanged in the imaging table 1a according to the first embodiment illustrated in FIG. 1. The radiation source 4 is arranged such that the radiation source 4 can irradiate the radiation towards the bucky apparatus 13 (such that the optical axis of the radiation becomes perpendicular to the second surface 132 of the bucky apparatus 13). When the setting is made in this way, the standing position imaging can be performed on the human subject P standing along the second surface 132 of the bucky apparatus 13.

When performing the recumbent position imaging, as illustrated in FIGS. 3A and 3B, the relative angle between the top plate 14 and the bucky apparatus 13 is set to become 0 degree. Further, the bucky apparatus 13 is set to overlap on the upper side of the top plate 14, and the second surface 132 of the bucky apparatus 13 is set to be substantially horizontal and to face to the upper direction. In this case, the support unit 12 is set in the orientation in which the straight line passing through the two supporters 15 becomes horizontal, and the top plate 14 is set in the orientation in which its first surface 141 becomes substantially horizontal (the orientation in which the second surface 132 of the bucky apparatus 13 overlapping on the upper side becomes substantially horizontal). Then, the radiation source 4 is arranged above the bucky apparatus 13 and the top plate 14 such that the radiation source 4 can downwardly irradiate the radiation. That is, the radiation source 4 is arranged such that the optical axis of the radiation to be irradiated becomes perpendicular to the second surface 132 of the bucky apparatus 13. When the setting is made in this way, the recumbent position imaging can be performed on the human subject P on the second surface 132 of the bucky apparatus 13.

When performing the lateral recumbent position imaging, as illustrated in FIGS. 3C and 3D, the setting is made such that the first surface 141 of the top plate 14 is substantially horizontal and faces to the upper direction, and the first surface 131 of the bucky apparatus 13 becomes perpendicular. That is, the angle formed between the top plate 14 and the bucky apparatus 13 is set to be 90 degrees. The support unit 12 is set in the orientation in which the straight line passing through the two supporters 15 becomes horizontal. Then, the radiation source 4 is arranged such that the optical axis of the radiation becomes horizontal and perpendicular to the first surface 131 of the bucky apparatus 13, so as to be able to irradiate the radiation towards the first surface 131 of the bucky apparatus 13. When the setting is made in this way, the lateral recumbent position imaging can be performed on the human subject P on the first surface 141 (the top surface) of the top plate 14.

In order to change from the setting of the recumbent position imaging illustrated in FIGS. 3A and 3B to the setting of the lateral recumbent position imaging illustrated in FIGS. 3C and 3D, the bucky apparatus 13 may be rotated 90 degrees such that the side provided with the rotation mechanism 16 is located in the lower side, and the radiation imaging apparatus 3 to be installed in the bucky apparatus 13 may be reversed. An arrow C in FIG. 3C indicates the rotation direction of the bucky apparatus 13. In this way, according to the second embodiment, the setting can be changed between the recumbent position imaging and the lateral recumbent position imaging by rotating the bucky apparatus 13 with respect to the top plate 14, and reversing the radiation imaging apparatus 3 to be installed in the bucky apparatus 13. Then, according to the imaging table according to the second embodiment, the same effect as in the first embodiment can be achieved.

Third Embodiment

FIGS. 4A to 4D are diagrams schematically illustrating the setting of an imaging table 1c according to a third embodiment and the state of the human subject P in the case of performing the recumbent position imaging and in the case of performing the lateral recumbent position imaging by using the imaging table 1c. FIG. 4A and FIG. 4B are a transverse cross sections and a vertical cross sectional view in the case of performing the recumbent position imaging, respectively. FIG. 4C and FIG. 4D are a transverse cross sectional view and a vertical cross sectional view in the case performing the lateral recumbent position imaging, respectively.

In the imaging table 1c according to the third embodiment, the top plate 14 is connected to the two supporters 15 as in the second embodiment. Then, one long side of the top plate 14 and one long side of the bucky apparatus 13 are connected to each other via the rotation mechanism 16, and the top plate 14 and the bucky apparatus 13 can be relatively rotated about the one long sides or about the vicinity of the long sides. Note that while the configuration may be adopted in which the bucky apparatus 13 and the top plate 14 can be rotated 90 degrees in the second embodiment, the configuration is adopted in which the bucky apparatus 13 and the top plate 14 can be rotated 270 degrees in the third embodiment.

The setting in the case of performing the standing position imaging by using the imaging table 1c may be the same as the setting in the second embodiment. When performing the recumbent position imaging, as illustrated in FIGS. 4A and 4B, the relative angle between the bucky apparatus 13 and the top plate 14 is set to be 0 degree. Then, the setting is made such that the bucky apparatus 13 overlaps on the upper side of the top plate 14, and the second surface 132 of the bucky apparatus 13 becomes substantially horizontal and faces to the upper direction. In this case, the support unit 12 is set in the orientation in which the straight line passing through the two supporters 15 becomes horizontal. Then, the radiation source 4 is arranged above the bucky apparatus 13 and the top plate 14 such that the radiation source 4 can downwardly irradiate the radiation (such that the optical axis of the radiation becomes perpendicular to the second surface 132 (the top surface) of the bucky apparatus 13). When the setting is made in this way, the recumbent position imaging can be performed on the human subject P on the second surface 132 of the bucky apparatus 13.

When performing the lateral recumbent position imaging, as illustrated in FIGS. 4C and 4D, the setting is made such that the first surface 141 of the top plate 14 is substantially horizontal and faces to the upper direction, and the second surface 132 of the bucky apparatus 13 becomes perpendicular. In this case, the relative angle between the bucky apparatus 13 and the top plate 14 is 270 degrees (90 degrees). Additionally, the support unit 12 is set in the orientation in which the straight line passing through the two supporters 15 becomes horizontal. Then, the radiation source 4 is arranged such that the optical axis of the radiation becomes horizontal and perpendicular to the second surface 132 of the bucky apparatus 13, so as to be able to irradiate the radiation towards the second surface 132 of the bucky apparatus 13. When the setting is made in this way, the lateral recumbent position imaging can be performed on the human subject P on the first surface 141 (the top surface) of the top plate 14.

In order to change the setting from the recumbent position imaging illustrated in FIGS. 4A and 4B to the lateral recumbent position imaging illustrated in FIGS. 4C and 4D, the top plate 14 may be rotated 180 degrees so as to be reversed, and the bucky apparatus 13 may be rotated 270 degrees with respect to the top plate 14. An arrow D in FIG. 4C indicates the rotation direction of the bucky apparatus 13, and an arrow E indicates the rotation direction of the top plate 14. In this case, in either of the recumbent position imaging and the lateral recumbent position imaging, since the radiation is made incident from the second surface 132 side of the bucky apparatus 13, the radiation imaging apparatus 3 to be installed in the bucky apparatus 13 may not be reversed. However, since the surface of the top plate 14 on which the human subject P gets on is interchanged, the getting off and getting on by the human subject P is required. In this way, according to the imaging table 1c according to the third embodiment, the same effect as in the first embodiment can be achieved.

Fourth Embodiment

Figure 5A:
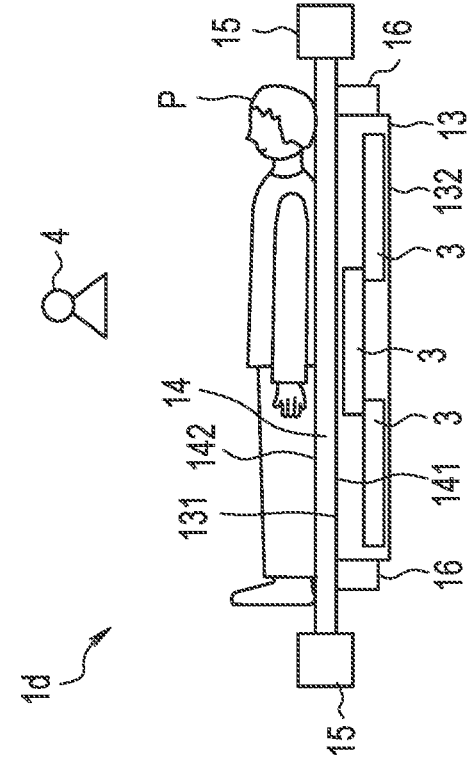
FIGS. 5A, 5B, 5C and 5D are schematic diagrams illustrating exemplary configurations of the imaging table according to a fourth embodiment.
Figure 5C:
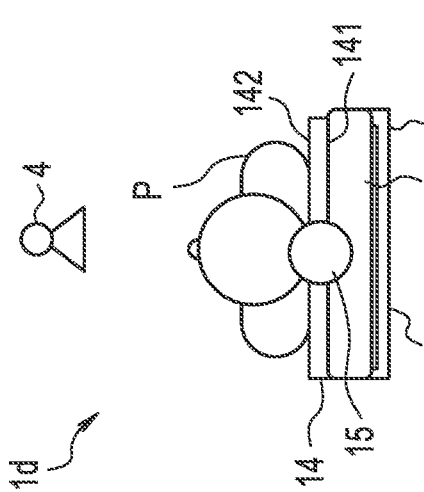
Figure 5B:
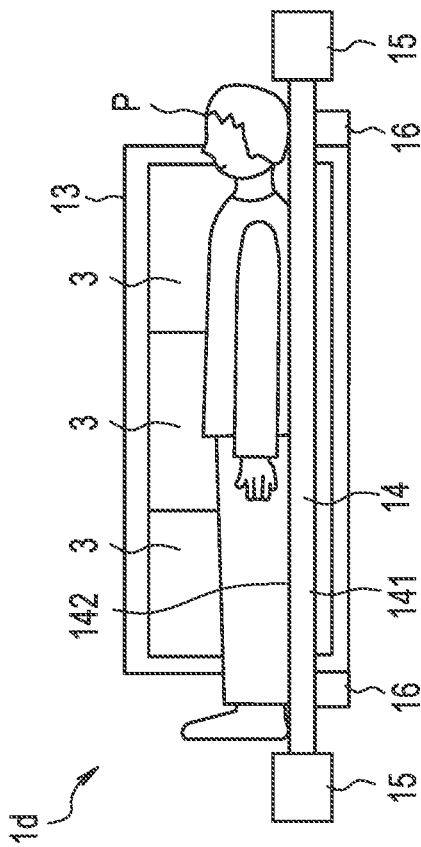
Figure 5D:
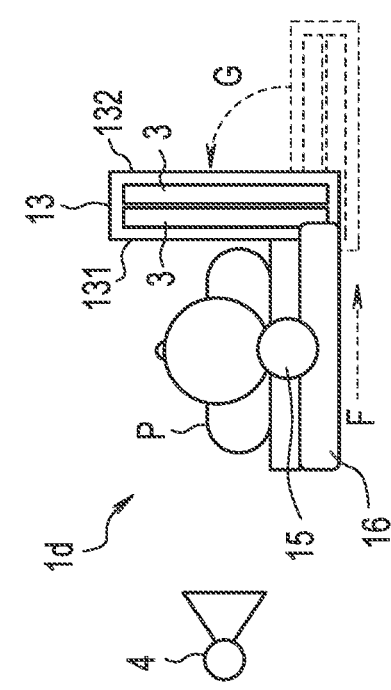

FIGS. 5A to 5D are diagrams schematically illustrating the setting of an imaging table 1d according to a fourth embodiment and the state of the human subject P in the case of performing the recumbent position imaging and in the case of performing the lateral recumbent position imaging by using the imaging table 1d. FIG. 5A and FIG. 5B are a transverse cross sections and a vertical cross sectional view in the case of performing the recumbent position imaging, respectively. FIG. 5C and FIG. 5D are a transverse cross sectional view and a vertical cross sectional view in the case performing the lateral recumbent position imaging, respectively.

In the imaging table 1d according to the fourth embodiment, the top plate 14 is connected to the two supporters 15. The top plate 14 and the bucky apparatus 13 are connected by the rotation mechanism 16 that can slidably move. Then, the bucky apparatus 13 and the top plate 14 are relatively movable in a short side direction, and can switch between the state where the bucky apparatus 13 and the top plate 14 are overlapped on each other when seen from the direction perpendicular to the second surface (the surface on which the human subject P gets on (the surface to be oriented to the subject)) of the top plate 14, and the state where the bucky apparatus 13 and the top plate 14 are shifted from each other. In the state where the bucky apparatus 13 and the top plate 14 are shifted from each other in the short side direction without overlapping on each other, the bucky apparatus 13 and the top plate 14 can be relatively rotated about one long sides (the long sides close to each other) or about the vicinity of the long sides. For example, either one of the top plate 14 and the bucky apparatus 13 is provided with a slide rail extending in the short side direction, and the rotation mechanism 16 is movably provided in the short side direction along this slide rail. Then, the rotation mechanism 16 is rotatably connected to the other one of the top plate 14 and the bucky apparatus 13.

When performing the standing position imaging by using the imaging table 1d, the relative angle between the bucky apparatus 13 and the top plate 14 is set to be 0 degree. Additionally, the support unit 12 is set in the orientation in which the straight line passing through the two supporters 15 becomes parallel to the up-and-down direction. Then, the setting is made such that the top plate 14 and the bucky apparatus 13 overlap on each other, and the second surface 142 of the top plate 14 is substantially perpendicular and oriented to the radiation source 4 side. The radiation source 4 is arranged to be able to irradiate the radiation towards the second surface 142 of the top plate 14. When the setting is made in this way, the standing position imaging can be performed on the human subject P standing along the second surface 142 of the top plate 14. That is, in the setting for the case of performing the standing position imaging by using the imaging table 1d according to the fourth embodiment, the orientations of and positional relationship between the bucky apparatus 13 and the top plate 14 are the same as those in the first embodiment.

When performing the recumbent position imaging, as illustrated in FIGS. 5A and 5B, the relative angle between the top plate 14 and the bucky apparatus 13 is set to be 0 degree. Then, the setting is made such that the top plate 14 overlaps on the upper side of the bucky apparatus 13, and the second surface 142 of the top plate 14 is substantially horizontal and faces to the upper direction. In this case, the support unit 12 is set in the orientation in which the straight line passing through the two supporters 15 becomes horizontal. Then, the radiation source 4 is arranged above the bucky apparatus 13 and the top plate 14 such that the radiation source 4 can downwardly irradiate the radiation. When the setting is made in this way, the recumbent position imaging can be performed on the human subject P on the second surface 132 (the top surface) of the bucky apparatus 13.

When performing the lateral recumbent position imaging, as illustrated in FIGS. 5C and 5D, the relative angle between the top plate 14 and the bucky apparatus 13 is set to be 90 degrees. Specifically, the second surface 142 of the top plate 14 is substantially horizontal and faces to the upper direction, and the first surface 131 of the bucky apparatus 13 is set to become perpendicular. In this case, the support unit 12 is set in the orientation in which the straight line passing through the two supporters 15 becomes horizontal. Then, the radiation source 4 is arranged such that the optical axis of the radiation becomes horizontal and perpendicular to the incident surface of the bucky apparatus 13, so as to be able to irradiate the radiation towards the first surface 131 of the bucky apparatus 13. When the setting is made in this way, the lateral recumbent position imaging can be performed on the human subject P on the second surface 142 (the top surface) of the top plate 14.

In order to change from the setting of the recumbent position imaging illustrated in FIGS. 5A and 5B to the setting of the lateral recumbent position imaging illustrated in FIGS. 5C and 5D, the bucky apparatus 13 may be moved in the short side direction to be shifted from the top plate 14, and may be rotated 90 degrees with respect to the top plate 14. An arrow F and an arrow G in FIG. 5C illustrate the moving direction and the rotation direction of the bucky apparatus 13, respectively. In this case, in either of the recumbent position imaging and the lateral recumbent position imaging, since the radiation is made incident from the first surface 131 side of the bucky apparatus 13, the radiation imaging apparatus 3 to be installed in the bucky apparatus 13 may not be reversed. In this way, according to the imaging table 1d according to the fourth embodiment, the same effect as in the first embodiment can be achieved. Additionally, in either of the recumbent position imaging and the lateral recumbent position imaging, the human subject P gets on the second surface 142 of the top plate 14. Thus, the getting off and getting on by the human subject P is not required. Note that though the configuration is adopted in which the top plate 14 is connected to the two supporters 15 in the present embodiment, the configuration may be adopted in which the rotation mechanism 16 is connected to and supported by the two supporters 15.

Fifth Embodiment

Figure 6A:
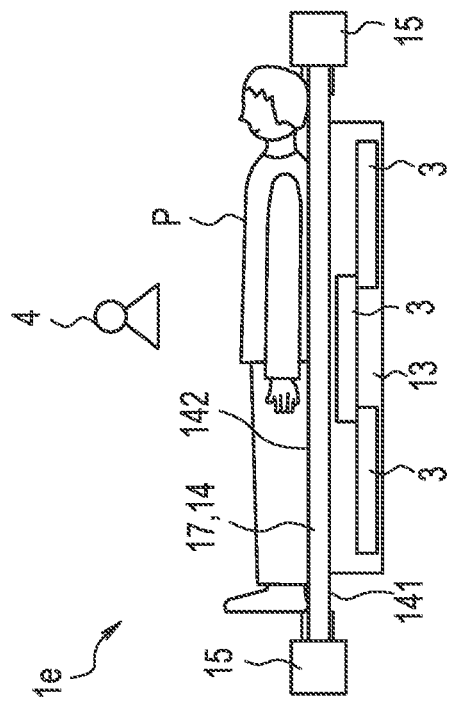
FIGS. 6A, 6B, 6C and 6D are schematic diagrams illustrating exemplary configurations of the imaging table according to a fifth embodiment.
Figure 6B:
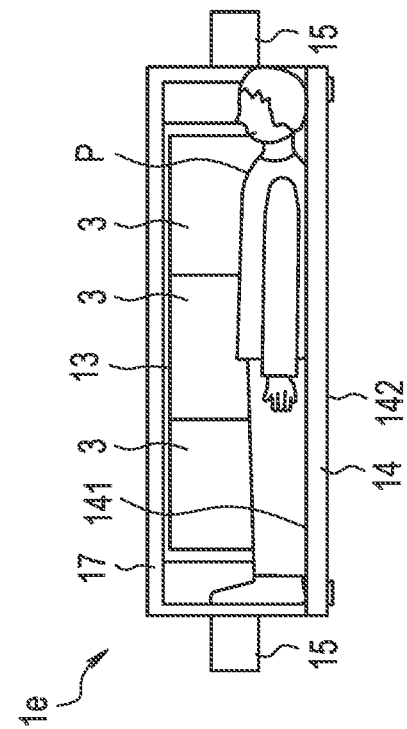
Figure 6C:
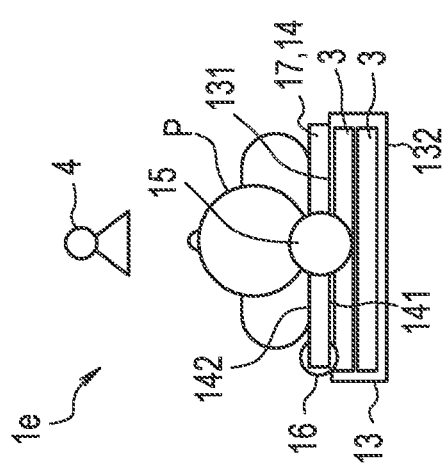
Figure 6D:
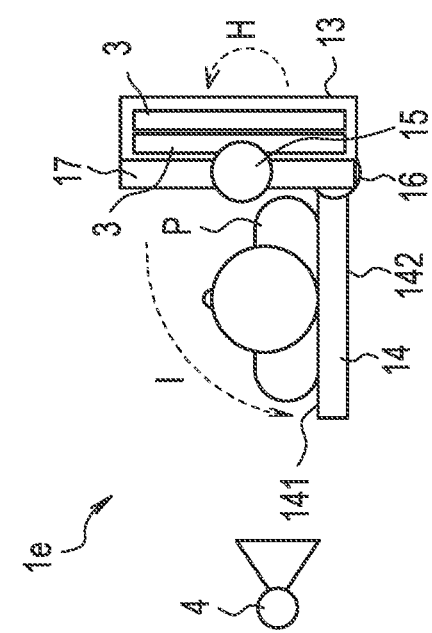

FIGS. 6A to 6D are diagrams schematically illustrating the setting of an imaging table 1e according to a fifth embodiment and the state of the human subject P in the case of performing the recumbent position imaging and in the case of performing the lateral recumbent position imaging by using the imaging table 1e. FIG. 6A and FIG. 6B are a transverse cross sections and a vertical cross sectional view in the case of performing the recumbent position imaging, respectively. FIG. 6C and FIG. 6D are a transverse cross sectional view and a vertical cross sectional view in the case performing the lateral recumbent position imaging, respectively.

The imaging table 1e further includes a holding frame 17. The holding frame 17 is fixed to the bucky apparatus 13, connected to the two supporters 15, and connected to the rotation mechanism 16. That is, the holding frame 17 is rotatably supported by the support unit 12 via the two supporters 15, and rotatably supports the top plate 14 via the rotation mechanism 16. Although the configuration of the holding frame 17 is not particularly limited, for example, it is possible to apply a picture-frame-like configuration in which a substantially rectangular opening is provided, and the top plate 14 can be inserted into the inner circumference of the opening, and a substantially "C" shaped configuration in which one side of the four sides is not provided with a member. Then, the top plate 14 and the holding frame 17 are relatively rotated by the rotation mechanism 16 about their respective long sides or about the vicinity of the long sides. However, the configuration of the holding frame 17 is not particularly limited. The holding frame 17 may be fixed to the bucky apparatus 13, and may be relatively rotatable with respect to the top plate 14.

When performing the standing position imaging by using the imaging table 1e, the relative angle between the bucky apparatus 13 and the top plate 14 is set to be 0 degree. Then, the second surface 142 of the top plate 14 is set to be oriented to the radiation source 4 side. In this case, the support unit 12 is set such that the straight line passing through the two supporters 15 become substantially perpendicular, so that the long length directions of the bucky apparatus 13 and the top plate 14 become parallel to the up-and-down direction. The radiation source 4 is arranged to be able to irradiate the radiation towards the top plate 14. When the setting is made in this way, the standing position imaging of the human subject P standing along the second surface 142 of the top plate 14 can be performed.

When performing the recumbent position imaging, as illustrated in FIGS. 6A and 6B, the relative angle between the top plate 14 and the bucky apparatus 13 is set to be 0 degree. Then, the setting is made such that the top plate 14 overlaps on the upper side of the bucky apparatus 13, and the second surface 142 of the top plate 14 becomes substantially horizontal and faces to the upper direction. In this case, the support unit 12 is set in the orientation in which the straight line passing through the two supporters 15 becomes horizontal, and the upper surface of the bucky apparatus 13 is set in the horizontal orientation. The radiation source 4 is arranged above the top plate 14 so as to be able to downwardly irradiate the radiation. When the setting is made in this way, the recumbent position imaging can be performed on the human subject P on the second surface 142 (the top surface) of the top plate 14.

When performing the lateral recumbent position imaging, as illustrated in FIGS. 6C and 6D, the relative angle between the bucky apparatus 13 and the top plate 14 is set to be 90 degrees. Then, the setting is made such that the first surface 141 of the top plate 14 is substantially horizontal and faces to the upper direction, and the bucky apparatus 13 and the holding frame 17 become perpendicular in the state where the rotation mechanism 16 is located in the lower side thereof. In this case, the support unit 12 is set in the orientation in which the straight line passing through the two supporters 15 becomes horizontal. The radiation source 4 is arranged such that the optical axis of the radiation becomes horizontal and perpendicular to the first surface 131 of the bucky apparatus 13, so as to be able to irradiate the radiation towards the first surface 131 of the bucky apparatus 13. When the setting is made in this way, the lateral recumbent position imaging can be performed on the human subject P on the first surface 141 (the top surface) of the top plate 14.

In order to change from the setting of the recumbent position imaging illustrated in FIGS. 6A and 6B to the setting of the lateral recumbent position imaging illustrated in FIGS. 6C and 6D, the bucky apparatus 13 and the holding frame 17 may be rotated 90 degrees such that the rotation mechanism 16 is located in the lower side thereof, and the top plate 14 may be rotated 90 degrees with respect to the bucky apparatus 13 and the holding frame 17. An arrow H in FIG. 6C indicates the rotation direction of the bucky apparatus 13, and an arrow I indicates the rotation direction of the top plate 14. Note that, in either of the recumbent position imaging and the lateral recumbent position imaging, since the radiation is made incident from the first surface 131 side of the bucky apparatus 13, the radiation imaging apparatus 3 to be installed in the bucky apparatus 13 may not be reversed. In this way, according to the imaging table 1e according to the fifth embodiment, the same effect as in the first embodiment can be achieved.

Radiation Imaging System

Figure 7:
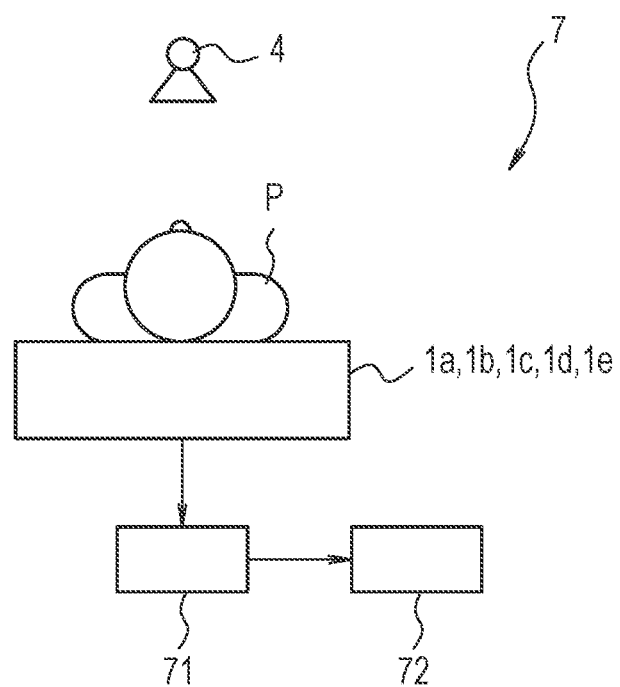
FIG. 7 is a schematic diagram illustrating an exemplary configuration of a radiation imaging system.

FIG. 7 is a diagram schematically illustrating an exemplary configuration of a radiation imaging system 7 according to one embodiment of the present invention. The radiation imaging system 7 includes, for example, the imaging table 1a, 1b, 1c, 1d or 1e according to the respective embodiments of the present invention, a control apparatus 71 including an image processor, etc., a display unit 72 including a display, etc., and the radiation source 4 for generating the radiation. The radiation source 4 may be movable depending on the arrangement of the bucky apparatus 13 of the imaging table 1a, 1b, 1c, 1d or 1e. The radiation (for example, X rays) emitted from the radiation source 4 penetrates the human subject P who is the subject, and is incident on the radiation imaging apparatus 3 installed in the bucky apparatus 13 of the imaging table 1a, 1b, 1c, 1d or 1e. Then, the radiation imaging apparatus 3 detects the radiation including the information of the inside of the body of the human subject P, and generates the image data of a radiation image. The control apparatus 71 performs predetermined signal processing on the image data of the radiation image obtained in this manner, and generates new image data. For example, the control apparatus 71 combines the image data generated by each of a plurality of radiation imaging apparatuses 3 installed in the bucky apparatus 13, and generates one long-length image data. This image data is displayed on the display unit 72.

According to the above-described embodiments of the present invention, it is possible to correspond to the methods of radiation imaging, and to facilitate the setting of the radiation imaging table according to the methods of radiation imaging.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2017-216311, filed Nov. 9, 2017 which is hereby incorporated by reference herein in its entirety.

What is claimed is:

1. An imaging table comprising:
a bucky apparatus to which a radiation imaging apparatus is installed;
a top plate connected to the bucky apparatus configured to allow a subject to get on the top plate;
a rotation mechanism arranged to connect the bucky apparatus and the top plate to each other in a relatively rotatable manner about a first axis;
a supporter arranged to rotably support the bucky apparatus about a second axis parallel to the first axis of relative rotation between the bucky apparatus and the top plate by the rotation mechanism; and
a support unit arranged to hold the supporter,
wherein the support unit is rotatable about a third axis perpendicular to the first axis.

2. The imaging table according to claim 1, wherein the bucky apparatus and the top plate are configured to be switched, by relatively rotating the bucky apparatus and the top plate by the rotation mechanism, between a state where a surface of the bucky apparatus on a side from which radiation is made incident is parallel to a surface of the top plate on a side oriented to the subject, and the bucky apparatus and the top plate are overlapped on each other, and a state where the surface of the bucky apparatus on the side from which the radiation is made incident is perpendicular to the surface of the top plate on the side oriented to the subject.

3. The imaging table according to claim 1, wherein the top plate has an elongated shape, and
the bucky apparatus and the top plate are relatively rotatable about one long side of the top plate by the rotation mechanism.

4. The imaging table according to claim 1, wherein the bucky apparatus and the top plate are relatively movable such that switching is made between a state where the bucky apparatus and the top plate are overlapped on each other and a state where the bucky apparatus and the top plate are shifted from each other, when seen from a direction perpendicular to the surface of the bucky apparatus from which the radiation is made incident and the surface of the top plate oriented to the subject, in a state where the surface of the bucky apparatus from which the radiation is made incident is parallel to the surface of the top plate oriented to the subject, and
the bucky apparatus and the top plate are relatively rotatable by the rotation mechanism in a state where the top plate is shifted in the short side direction.

5. The imaging table according to claim 1, further comprising a support column arranged to rotatably support the support unit via a rotatory part about the third axis,
wherein the support unit is supported by the support column to be movable in an up-and-down direction.

6. The imaging table according to claim 1, wherein the top plate and the bucky apparatus have elongated shapes, and
the length of top plate is shorter than the length of the bucky apparatus in a long length direction and a short length direction.

7. The imaging table according to claim 6, wherein a total length of the top plate and the rotation mechanism is substantially equal to the length of the bucky apparatus in the long length direction and the short length direction.

8. A radiation imaging system comprising:
the imaging table according to claim 1;
a radiation source arranged to irradiate radiation towards the radiation imaging apparatus; and
a control apparatus configured to process a signal generated by the radiation imaging apparatus.

9. The radiation imaging system according to claim 8, wherein the radiation imaging system is configured to perform one shot long-length imaging in which imaging is performed by one time radiation irradiation by using a plurality of radiation imaging apparatuses and one radiation source.

10. The radiation imaging system according to claim 9, wherein the radiation source is movable in response to the arrangement of the bucky apparatus.

11. The imaging table according to claim 1, wherein the bucky apparatus has an elongated shape with a line symmetry about the second axis.

12. The imaging table according to claim 11, wherein the supporter is arranged to an end of an arm of the support unit, and the bucky apparatus is configured to rotate about the second axis.

* * * * *